United States Patent [19]

Enders

[11] 4,036,850
[45] July 19, 1977

[54] 1-ARYL-5-ALKYLIDENE,2,4-DIOXO-IMIDAZOLIDINES AND PROCESS THEREFOR

[75] Inventor: Edgar Enders, Cologne, Germany

[73] Assignee: Bayer Aktiengesellschaft, Leverkusen, Germany

[21] Appl. No.: 555,661

[22] Filed: Mar. 5, 1975

[30] Foreign Application Priority Data

Mar. 26, 1974    Germany .............................. 2414613

[51] Int. Cl.$^2$ .......................................... C07D 233/04
[52] U.S. Cl. .......................... 260/309.5; 260/553 A; 260/553 E; 260/247.2 R; 424/273
[58] Field of Search ....................................... 260/309.5

[56] References Cited

FOREIGN PATENT DOCUMENTS

| 45-24776 | 8/1970 | Japan ................................ 260/309.5 |
| 45-31959 | 10/1970 | Japan ................................ 260/309.5 |

*Primary Examiner*—Ethel G. Love
*Attorney, Agent, or Firm*—Burgess, Dinklage & Sprung

[57] ABSTRACT

1-aryl-5-alkylidene-2,4-dioxo-imidazolidine and N-aryl-N'-(2,3-dihalogen alkanoyl)-ureas are disclosed. The latter compounds are reacted with an alkali metal alkoxide in a solvent at a temperature in the range of between 20° C and the boiling temperature of the solvent to produce the dioxo-imidazolidenes, which may be used as herbicides, fungicides, bactericides, nematocides or as coccidiostatics.

12 Claims, No Drawings

1-ARYL-5-ALKYLIDENE,2,4-DIOXO-IMIDAZOLIDINES AND PROCESS THEREFOR

This invention relates to new 1-aryl-5-alkylidene-2,4-dioxo-imidazolidines.

SUMMARY

The 1-aryl-5-alkylidene-2,4-dioxo-imidazolidines of the invention correspond to the general formula (I):

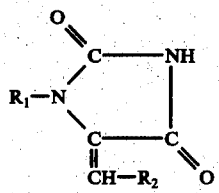

in which $R_1$ represents an aryl radical which may be substituted either once or several times by halogen radicals, $C_1$–$C_6$ alkyl radicals, $C_5$ or $C_6$ cycloalkyl radicals, $C_1$ or $C_2$ halogen alkyl radicals, $C_1$–$C_6$ alkoxy radicals, $C_1$–$C_6$ thioalkyl radicals and sulphoxide radicals, $C_1$–$C_6$ alkyl sulphono radicals, $C_1$–$C_4$ mono- or di-alkyl and diaryl aminoalkyl radicals, $C_1$–$C_6$ acyl amino radicals, cyclic amine radicals, in which the amine nitrogen is part of a 5-membered or 6-membered heterocycle which, in addition, may contain further hetero atoms such as nitrogen, oxygen or sulphur as ring members, cyano radicals, nitro radicals, acetyl radicals, aldehyde radicals, phenyl radicals, phenoxy radicals, halogen phenoxy radicals, nitrophenoxy radicals, phenyl thio radicals, benzyl radicals, anilino radicals, benzyl sulphonyl radicals, phenyl sulphonyl radicals and halogen-benzene sulphonyl radicals; and $R_2$ represents hydrogen or a lower $C_1$–$C_6$ alkyl radical.

Examples of the groups $R_1$ and $R_2$ as defined above are given in the description of the process, aryl radicals being preferably aromatic hydrocarbon radicals with 6 to 10 carbon atoms, more especially phenyl and naphthyl. A preferred group of 1-aryl-5-alkylidene-2,4-dioxo-imidazolidines corresponds to the general formula I wherein $R^1$ is preferably naphthyl or the group

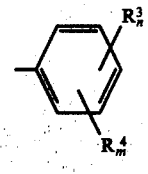

wherein $R^3$ represents a radical selected from the group of hydroxy, nitro, halogen, $C_1$-$C_3$-alkyl, $C_1$-$C_3$-alkoxy, and substituted or unsubstituted phenoxy, $R^4$ represents a radical selected from the group of halogen and $C_1$-$C_3$-alkyl and n and m are same or different, each representing a number selected of the group of 0,1,2 or 3 provided that the sum of n and m is not greater than 5.

The 1-aryl-5-alkylidene-2,4-dioxo-imidazolidines are obtained by reacting N-aryl-N′-(2,3-dihalogen alkanoyl) ureas

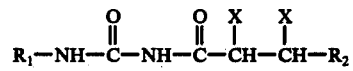

in which $R_1$ and $R_2$ have the same meaning as in formula (I), and

X represents chlorine and/or bromine, with alkali metal alkoxides in the presence of a solvent at temperatures of between 20° C and the boiling temperature of the solvent.

DESCRIPTION

The reaction is illustrated by way of example in the following with reference to the reaction of N-phenyl-N′-(2,3-dibromo propionyl)-urea and potassium tert.-butylate, which gives 1-phenyl-5-methylene-2,4-dioxo-imidazolidine:

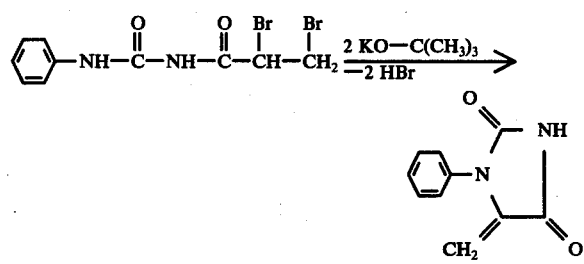

According to Org. Synth., Coll. Vol II (1943), pages 10 and 515, 2,3-dibromo succinic acid reacts to form acetylene dicarboxylic acid and 2,3-dibromo-5-phenyl propionic acid ethyl ester reacts to form phenyl propiolic acid in the presence of alcoholic potassium hydroxide, the reactions being accompanied by the elimination of 2 mols of hydrogen bromide. It is also known that alkine carboxylic acids, for example propiolic acid, undergo addition reactions at the 3-position (H. E. Rodd, Chemistry of Carbon Compounds, Vol. IA, page 642).

Accordingly, the fact that 1-aryl-5-alkylidene-2,4-dioxoimidazolidines are formed by the process according to the invention is surprising because it had been expected that 2mols of hydrogen halide would be eliminated from the N-aryl-N′-(2,3-dihalogen propionyl)-ureas to form N-aryl-N′-propiolyl ureas which in turn were expected to form a 6-membered ring by cyclisation through the 3-position, which is preferred for addition reactions.

The process according to the invention may be carried out, for example, with the following N-aryl-N′-(2,3-dihalogen acyl)-ureas as starting materials which may be obtained by any of the processes described hereinafter:

N-phenyl-N′-(2,3-dibromopropionyl)-urea
N-(2,4-dichlorophenyl-N′-(2,3-dibromopropionyl-urea
N-(4-nitrophenyl)-N′-(2,3-dibromopropionyl)-urea
N-(4-ethoxyphenyl)-N′-(2,3-dibromopropionyl)-urea
N-(naphthyl-(1))-N′(2,3-dibromopropionyl)-urea
N-phenyl-N′-(2,3-dichloropropionyl)-urea
N-(2-chlorophenyl)-N′-(2,3-dichloropropionyl)-urea
N-(2-chloro-4-fluorophenyl)-N′-(2,3-dichloropropionyl)-urea
N-(2,4-dichlorophenyl)-N′-(2,3-dichloropropionyl)-urea N-(2-chloro-4-bromophenyl)-N'-(2,3-dibromopropionyl)-urea
N-(2,6-dichlorophenyl)-N'-(2,3-dichloropropionyl)-urea
N-(3,5-dichlorophenyl-N'-(2,3-dibromopropionyl)-urea
N-(3,5-dichloro-4-ethylmercypto-phenyl)-N'-(2,3-dibromopropionyl)-urea
N-(3,5-dibromophenyl)-N'-(2,3-dibromopropionyl)-urea
N-(3,5-dichloro-4-iodophenyl)-N'-(2,3-dichloropropionyl)-urea
N-(2-methyl-4-chlorophenyl)-N'-(2,3-dichloropropionyl)-urea
N-(2-ethyl-4-bromophenyl)-N'-(2,3-dichloropropionyl)-urea
N-(2,6-dimethylphenyl)-N'-(2,3-dichloropropionyl)-urea
N-(4-chloro-3,5-dimethylphenyl)-N'-(2,3-dibromopropionyl)-urea
N-(2,6-diisopropylphenyl)-N'-(2,3-dibromopropionyl)-urea
N-(3-chloro-4-dimethylaminophenyl)-N'-(2,3-dichloropropionyl)-urea
N-(3,5-dichloro-4-acetylaminophenyl)-N'-(2,3-dibromopropionyl)-urea
N-(3,5-dichloro-4-hydroxyphenyl)-N'-(2,3-dibromopropionyl)-urea
N-(2,3,5,6-tetrachlorophenyl)-N'-(2,3-dibromopropionyl)-urea
N-(2-chloro-4-ethoxyphenyl)-N'-(2,3-dichloropropionyl)-urea
N-(2-chloro-5-trifluoromethylphenyl)-N'-(2,3-dibromopropionyl)-urea
N-(4-chloro-3-dimethylamidosulphonyl-phenyl)-N'-(2,3-dicloro-propionyl)-urea
N-(3-dimethylamidocarbonyl-phenyl)-N'-(2,3-dibromopropionyl)-urea
N-(3-methyl-4-methallyloxyphenyl)-N'-(2,3-dbromopropionyl)-urea
N-(3-chloro-4-methanosulphonyloxyphenyl)-N'-(2,3-dibromopropionyl)-urea
N-(2-chloro-5-cyanophenyl)-N'-(2,3-dibromopropionyl)-urea
N-(2-chloro-5-chloromethylsulfonyl-phenyl-)-N'-(2,3-dibromopropionyl)-urea
N-(2-chloro-4-nitrophenyl)-N'-(2,3-dichloropropionyl)-urea
N-(4-bromo-3-chlorophenyl)-N'-(2,3-dichloropropionyl)-urea
N-(3,4-dimethoxyphenyl)-N'-(2,3-dibromopropionyl)-urea
N-(4-chloro-2,5-diethoxyphenyl)-N'-(2,3-dichloropropionyl)-urea
N-(4-phenoxyphenyl)-N'-(2,3-dibromopropionyl)-urea
N-(3,5-dichloro-4-(4'-chlorophenoxy)-phenyl)-N'-(2,3-dibromopropionyl)-urea
N-(3,5-dimethyl-(4'-bromophenoxy)-phenyl)-N'-(2,3-dibromopropionyl)-urea
N-(3-methyl-5-chloro-4-(4'-cyanophenoxy)-phenyl)-N'-(2,3-dibromopropionyl)-urea
N-(3-chloro-4-(4'-chlorophenylthio-phenyl)-N'-(2,3-dibromopropionyl)-urea
N-(3,5-dibromo-4-phenylthiophenyl)-N'-(2,3-dibromopropionyl)-urea
N-[4-(4'-chlorophenylsulphonyl)-phenyl]-N'-(2,3-dibromopropionyl)-urea
N-[4-(4'-chloroanilino)-3,5-dichlorophenyl]-N'-(2,3(2,3-dichloropropionyl)-urea
N-[4-(2',4(-diclorobenzoyl)-3-chlorophenyl]-N'-(2,3-dibromopropionyl)-urea
N-(4-(4'-clorobenzoylamino)-3,5-dichlorophenyl)-N'-(2,3-dibromopropionyl)-urea
N-(1-chloro-2-naphthyl)-N'-(2,3-dibromopropionyl)-urea
N-(5-methoxy-1-naphthyl)-N'-(2,3-dibromopropionyl)-urea
N-(5,6,7,8-tetrahydro-1-1-naphthyl)-N'-(2,3-dicloropionyl)-urea
N,N-(phenylene-(1,3-bis-N',N'-(2,3-dibromopropionyl)-urea
N-(3,4-dichlorophenyl)-N'-(2,3-dibromobutyryl)-urea
N-(2,4-dichlorophenyl)-N'-(2,3-dibromobutyryl)-urea
N-(4-chloro-2-methylphenyl)-N'-(2,3-dichlorobutyryl)-urea
N-(3,5-dichloro-4-(4'-chlorophenoxy)-phenyl)-N'-(2,3-dibromobutyryl)-urea
N-(3,5-dibromo-4-(4'-chlorophenylthio)-phenyl)-N'-(2,3-dichlorobutyryl)-urea
N-(3,4,5-trimethoxyphenyl)-N'-(2,3-dibromobutyryl)-urea A preferred group of the N-aryl-N'-(2,3-dihalogen acyl)-ureas as starting materials corresponds to the general formula II, wherein
R¹ is preferably naphthyl or the group

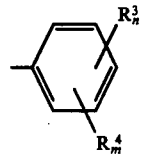

wherein R³ represents a radical selected from the group of hydroxy, nitro, halogen, $C_1$—$C_3$—alkyl, $C_1$—$C_3$—alkoxy, and substituted or unsubstituted phenoxy R⁴ represents a radical selected from the group of halogen and $C_1$—$C_3$—alkyl and n and m are same or different, each representing a number selected from the group of 0,1,2 or 3 provided, that the sum of n and m is not greater than 5.

Preferred alkali metal alkoxides are the sodium or potassium alkoxides of lower $C_1$—$C_6$—alkanols and $C_5$—$C_6$—acycloalkanols, for example methanol, ethanol, isopropanol, butanol, tert.-butanol and cyclohexanol, preferably potassium tert.-butylate. Examples of suitable solvents are alcohols such as, $C_1$—$C_6$— alkanols and $C_5$—$C_6$—cycloalkanols, for example, methanol, ethanol, isopropanol, butanol and tert.-butanol, and ethers such as alkyl ethers with 4 to 8 carbon atoms, e.g. diisopropyl ether, di-n-butyl-ether, 1,2-dimethoxy ethan, and cyclic ethers, for example, tetrahydrofuran or dioxan. The preferred solvent is the alcohol used for the preparation of the alkali metal alkoxide.

The reaction may, for example, be carried out by reacting from 2 to 4 mols, preferably from 2 to 3.5 mols, of alkali metal alkoxide with 1 mol of N-aryl-N'-(2,3-dihalogen acyl)-urea in 1000 ml to 8000 ml, preferably in 2000 to 6000 ml, of solvent. The reaction is carried out at temperatures in the range of from 20° C to the boiling temperature of the solvent, and preferably at temperatures in the range of from 50° C to 120° C. In one particular embodiment of the process according to the invention, the reaction may be completed by distilling off the solvent and heating the residue under normal pressure or in vacuo to temperatures in the range of from 60° C to 180° C, preferably to temperatures in the range of from 80° C to 140° C.

In one preferred embodiment of the process according to the invention, the N-aryl-N'-(2,3-dihalogen alkanol)-urea of general formula (II) is reacted with 2 to 4 mols, more especially 2 to 3.5 mols, of potassium tert.-butylate in tert.-butanol as solvent at temperatures in the range of from 20° to 180° C and preferably at temperatures in the range of from 60° to 150° C.

On completion of the reaction, the 1-aryl-5-methylene-2,4-dioxo-imidazolidines formed accumulate in admixture with the alkali metal halide formed. They may be dissolved in water, optionally in the presence of sodium hydroxide, subsequently filtered and then precipitated with acids, for example with dilute hydrochloric acid or dilute acetic acid, hydrochloric acid or sulphuric acid. if it is not possible under these conditions to dissolve the 1-aryl-5-methylene-2,4-dioxoimidazolidines, they are digested with water at pH 3 to 7 in order to remove the alkali metal halides, filtered, dried and recrystallised from a suitable solvent.

The following are examples of the 1-aryl-5-methylene-2,4-dioxo-imidazolidines obtainable in accordance with the invention:

1-phenyl-5-methylene-2,4-dioxo-imidazolidine
1-(3,4-dichlorophenyl)-5-methylene-2,4-dioxo-imidazolidine
1-(4-nitrophenyl)-5-methylene-2,4-dioxo-imidazolidine
1-(4chlorophenyl)-5-methylene-2,4-dioxo-imidazolidine
1(4-ethoxyphenyl)-5-methylene-2,4-dioxo-imidazolidine
1-naphthyl-(1)-5-methylene-2,4-dioxo-imidazolidine
1-(2-chlorophenyl)-5-methylene-2,4-dioxo-imidazolidine
1-(4-bromophenyl)-5-methylene-2,4-dioxo-imidazolidine
1-(4-iodophenyl)-5-methylene-2,4-dioxo-imidazolidine
1-(3-nitrophenyl)-5-methylene-2,4-dioxo-imidazolidine
1-(2-nitrophenyl)-5-methylene-2,4-dioxo-imidazolidine
1-(3,5-dichlorophenyl)-5-methylene-2,4-dioxo-imidazolidine
1-(2,6-dichlorophenyl)-5-methylene-2,4-dioxo-imidazolidine
1-(4-hydroxyphenyl)-5-methylene-2,4-dioxo-imidazolidine 1-(3,5-dichloro-4-hydroxyphenyl)-5-methylene-2,4-dioxoimidazolidine
1-(3,5-dichloro-4cyanophenyl)-5-methylene-2,4-dioxoimidazolidine
1-(3,5-dibromophenyl)-5methylene-2,4-dioxo-imidazolidine
1-(3,5-bis-trifluoromethylphenyl)-5-methylene-2,4-dioxoimidazolidine
1-(3,5-dichloro-4-thiocyanophenyl)-5-methylene-2,4-dioxoimidazolidine
1-(3,5-dichloro-4-ethylmercaptophenyl)-5-methylene-2,4-dioxo-imidazolidine
1(2,4-dimethylphenyl)-5-methylene-2,4-dioxo-imidazolidine
1-(2,6-diisopropylphenyl)-5-methylene-2,4-dioxo-imidazolidine
1-(2-methyl-4-chlorophenyl)-5-methylene-2,4-dioxo-imidazolidine
1-(4-chloro-3-diethylamidosulphonylphenyl)-5-methylene-2,4-dioxo-imidazolidine
1-(4-chloro-2-dimethylamidocarbonylphenyl)-5-methylene-2,4-dioxo-imidazolidine
1-(4-methanesulfonyloxy-3-chlorophenyl)-5-methylene-2,4-dioxo-imidazolidine
1-(2,4,5-trichlorophenyl)-5-methylene-2,4-dioxo-imidazolidine
1-(4-chloro-3,5-dimethylphenyl)-5-methylene-2,4-dioxoimidazolidine
1-(4-dimethylamino-3-chlorophenyl)-5-methylene-2,4-dioxoimidazolidine
1-(4-chloro-3-methoxycarbonylaminophenyl)-5-methylene-2,4-dioxo-imidazolidine
1(3,4-dimethoxyphenyl)-5-methylene-2,4-dioxo-imidazolidine
1-(3,4-methylenedioxyphenyl)-5-methylene-2,4-dioxo-imidazolidine
1-(3-methyl-4-methallyloxyphenyl)-5-methylene-2,4-dioxoimidazolidine
1-(4-chloro-2,5-diethoxyphenyl)-5-methylene-2,4-dioxoimidazolidine
1-(2-chloro-5-aldehydophenyl)-5-methylene-2,4-dioxoimidazolidine
1-(4-phenoxyphenyl)-5-methylene-2,4-dioxo-imidazolidine
1-[3-chloro-4-(4'-chlorophenoxy)-phenyl]-5-methylene-2,4-dioxo-imidazolidine 1-[3,5-dichloro-4-(4'-bromophenoxy)-phenyl]-5-methylene-2,4-dioxo-imidazolidine
1-[3,5-dimethyl-4-(4'-chlorophenoxy)-phenyl]-5-methylene-2,4-dioxo-imidazolidine
1-[3-chloro-5-methyl-4-(2',4'-dichlorophenoxy)-phenyl]-5-methylene-2,4-dioxo-imidazolidine
1[3,5-dichloro-4-(4'-cyanophenoxy)-phenyl]-5-methylene-2,4-dioxo-imidazolidine
1-[3,5-dibromo-4-(4'-nitrophenoxy)-phenyl]-5-methylene-2,4-dioxo-imidazolidine
1-[3-methyl-4-(4'-bromophenoxy)-phenyl]-5-methylene-2,4-dioxo-imidazolidine
1-[3,5-dichloro-4-(4'-iodophenoxy)-phenyl]-5-methylene-2,4-dioxo-imidazolidine
1-[3,5-dichloro-4-(4'-chlorophenoxy)-phenyl]-5-methylene-2,4-dioxo-imidazolidine
1-[3,5-dichloro-4-(3'-methyl-4'-methylmercaptophenoxy)-phenyl]-5-methylene-2,4-dioxo-imidazolidine
1-[3,5-dichloro-4-(3'-methyl-4'-dimethylaminophenoxy)-phenyl]-5-methylene-2,4-dioxo-imidazolidine
1-[3,5-dichloro-4-(2',6'-dimethylphenoxy)-phenyl]-5-methylene-2,4-dioxo-imidazolidine
1-[3,5-dichloro-4-(naphthyl-(2)-oxy)-phenyl]-5-methylene-2,4-dioxo-imidazolidine
1-[3-chloro-4-(4'-chlorophenylthio)-phenyl]-5-methylene-2,4-doxo-imidazolidine
1-[3,5-dimethyl-4-(4'-chlorophenylthio)-phenyl]-5-methylene-2,4-dioxo-imidazolidine
1-[3,5-dibromo-4-(4'-chlorophenylthio)-phenyl]-5-methylene-2,4-dioxo-imidazolidine
1-[3,5-dichloro-4-(4'-chloroanilino)-phenyl]-5-methylene-2,4-dioxo-imidazolidine
1-[3,5-dichloro-4-(4'-dimethylamino-anilino)-phenyl]-5-methylene-2,4-dioxo-imidazolidine
1-[3,5-dichloro-4-(4'-bromoanilino)-phenyl]-5-methylene-2,4-dioxo-imidazolidine
1-[3,5-dichloro-4-(4'-methoxyanilino)-phenyl]-5-methylene-2,4-dioxo-imidaxolidine
1-(4-nitrodiphenylyl)-5-methylene-2,4-dioxo-imidazolidine
1-[3,5-dicloro-4-(4'-hydroxy-3,5-di-tert.-butylphenyl)-phenyl]-5-methylene-2,4-dioxo-imidazolidine
1[5-chloro-4-(4'-chlorophenyl sulphonyl)-phenyl]-5-methylene-2,4-dioxo-imidazolidine 1-[3-chloro-4-(2',4'-dichlorobenzoyl)-phenyl]-5-methylene-2,4-dioxo-imidazolidine 1-[3-bromo-4-(4'-chlorobenzoylamino)-phenyl]-5-methylene-2,4-dioxo-imidazolidine 1[3,5-dimethyl-4(4'-chlorobenzoyl amino]-phenyl)-5-methylene-2,4-dioxo-imidazolidine 1-[3,5-dichloro-4-(4'-chlorobenzyloxy)-phenyl]-5-methylene-2,4-dioxo-imidazolidine 1-[4-(4'-dichlorobenzyl)-phenyl]-5-methylene-2,4-dioxo-imidazolidine 1-[1-chloronaphthyl-(2)]-5-methylene-2,4-dioxo-imidazolidine 1-[4-methoxynaphthyl-(1)]-5-(methylene2,4-dioxo-imidazolidine 1-[5,6,7,8-tetrahydro-naphthyl-(1)]-5-methylene-2,4-dioxoimidazolidine 1-(3,4-dichlorophenyl)-5-ethylidene-2,4-dioxo-imidazolidine 1-(2,4-dichlorophenyl)-5-ethylidene-2,4-dioxo-imidazolidine 1-(4-chloro-3-methylphenyl)-5-ethylidene-2,4-dioxo-imidazolidine 1-[3,5-dichloro-4-(4'-chlorophenoxy)-phenyl]-5-ethylidene-2,4-dioxo-imidazolidine 1-[3,5-dibromo-4-(4'-chlorophenylthio)-phenyl]5-ethylidene-2,4-dioxo-imidazolidine 1-(3,4,5-trimethoxyphenyl)-5-ethylidene-2,4-dioxo-imidazolidine The N-aryl-N'-(2,3-dihalogen alkanoyl)-ureas, which are reacted with the alkali metal alkoxides to form the 1-aryl-5-alkylideno-2,4-dioxo-imidazolidines, are obtained by reacting halogenated acyl isocyanates corresponding to the general formula (III):

in which
R$_2$ represents hydrogen or a C$_1$–C$_6$ alkyl radical, preferably methyl, and
X represents chlorine and/or bromine,
with primary aryl amines corresponding to the general formula (IV):

in which
R$_1$ has the same meaning as in formula (I), in the presence of a solvent described herein at a temperature in the range of from −20° C to +50° C. The reaction is illustrated by way of example with reference to the reaction of aniline with 2,3-dibromopropionyl isocyanate which yields N-phenyl-N'-(2,3-dibromopropionyl)-urea:

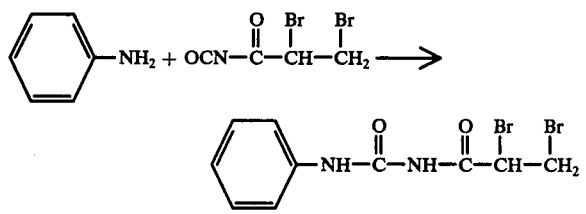

Halogenated acyl isocyanates of the kind used in the process according to the invention may be obtained by reacting α,β-unsaturated carboxylic acid amides, such as acrylic acid amide or crotonic acid amide, with halogens, preferably chlorine or bromine, to form 2,3-dihalogen carboxylic acid amides, and subsequently reacting the 2,3-dihalogen carboxylic acid amides with an excess of oxalyl chloride of as much as 200 mol %, based on the amide. The reaction may optionally be carried out without intermediate isolation of the 2,3-dihalogen carboxylic acid amide.

The 2,3-dihalogen alkanoyl isocyanates are preferably prepared in anhydrous, inert solvents. Suitable solvents are halogenated hydrocarbons such as dichloromethane, chloroform, tetrachloromethane, 1,2-dichlorethylene, aliphatic and aromatic hydrocarbons such as petrol, cyclohexane, isooctane, benzene, toluene, o-xylene, m-xylene, p-xylene, chlorinated benzene derivatives such as chlorobenzene and 1,2-dichlorobenzene, and others such as diisopropyl ether.

Addition of the halogen to the α,β-unsaturated carboxylic acid amide may be carried out, for example, at temperatures in the range of from −20° to +80° C, preferably at temperatures in the range of from −10° to +30° C and, more especially, at temperatures in the range of from −10° C to +20° C.

Reaction of the 2,3-dihalogen alkane carboxylic acid amide with oxalyl chloride may be carried out at a temperature in the range of from 20° C to 120° C, preferably at a temperature in the range of from 50° C to 100° C and more especially at a temperature in the range of from 60° C to 80° C.

The following dihalogen acyl isocyanates may be used in the process according to the invention: preferably 2,3-dichloro alkanoyl isocyanates and 2,3-dibromo alkanoyl isocyanates such as, for example, 2,3-dichloropropionyl isocyanate, 2,3-dibromopropionyl isocyanate, 2,3-dibromo butyryl isocyanate, 2,3-dichloro butyryl isocyanate, 2,3-dibromo-N-pentanoyl isocyanate and 2,3-dichloro-n-octanoyl isocyanate, particularly 2,3-dichloropropionyl isocyanate and 2,3-dibromopropionyl isocyanate.

The following aryl amines for example, preferably anilines or amino naphthalenes, which may be substituted either once or several times, may be reacted with the 2,3-dihalogen acyl isocyanates. The following substituents for R$_1$ are mentioned by way of example: halogens such as fluorine, chlorine, bromine and iodine, hydroxy, cyano, nitro, acetyl, aldehyde, phenyl, phenoxy, o-fluorophenoxy, m-fluorophenoxy, p-fluorophenoxy, o-chlorophenoxy, m-chlorophenoxy, p-chlorophenoxy, o-bromophenoxy, m-bromophenoxy, p-bromophenoxy, o-nitrophenoxy, m-nitrophenoxy, p-nitrophenoxy, phenylthio, 4-chlorophenylthio, 4-bromophenylthio, benzyl, anilino, 4-chloroanilino, 4-bromoanilino, benzoyl, o-benzene sulphonyl, m-benzene sulphonyl, p-benzene sulphonyl, o-halogen benzene sulphonyl, m-halogen benzene sulphonyl, p-halogen benzene sulphonyl, p-halogen benzene sulphinyl, C$_1$–C$_6$ alkyl, preferably methyl, ethyl, propyl, isopropyl and tert.-butyl, C$_5$–C$_6$-cycloalkyl, for example cyclohexyl, cyclohexenyl and cyclopentyl, C$_1$–C$_2$-halogen alkyl, for example trifluoromethyl, C$_1$–C$_6$-alkoxy, for example methoxy, ethoxy, butoxy, allyloxy and methallyloxy, C$_1$–C$_6$-thioalkyl, for example methyl thio, ethyl thio and alkyl thio, the thiocyano group, C$_1$–C$_4$-alkyl sulphonyl, for example methyl sulphonyl, chloromethyl sulphonyl, trichloromethyl sulphonyl and trifluoromethyl sulphonyl, ethyl sulphonyl C$_1$–C$_4$-alkyl sulphinyl, for example methyl sulphinyl, C$_1$–C$_4$-mono- or di-alkyl amino, for example dimethyl amino and diethyl amino, $C_1$-$C_6$-acyl amino, for example acetyl amino, chloroacetyl amino, propionyl amino, isobutyryl amino, $C_1$- $C_4$-alkoxy carbonyl amino, preferably methoxy carbonyl amino, ethoxy carbonyl amino, butoxy carbonyl amino, cyclic amine radicals, in which the amine nitrogen is part of a 5-membered or 6-membered heterocycle which, in addition, may contain further heterocyclic ring members such as N,O,S, for example pyrrolidino, 2-oxapyrrolidino, imidazoline and morpholino, $C_1$- $C_6$- alkyl- and aryl-sulphonyl oxy, for example methanosulphonyl oxy and benzosulphonyloxy, amidosulphonyl and mono- or di-$C_1$- $C_6$-alkyl- and aryl-amidosulphonyl, for example dimethyl amidosulphonyl, alkyl amidosulphonyl, butyl aminosulphonyl, peperidinosulphonyl, 4-chloroanilidosulphonyl, amidocarbonyl and mono- or di-$C_1$-$C_1$-alkyl amidocarbonyl, for example dimethyl amidocarbonyl, morpholinocarbonyl and methyl amidocarbonyl.

The following aryl amines may, for example, be used: aniline, 2-, 3- or 4-chloroaniline, the isomeric dichloranilines, for example 3,4-dichloraniline, 2,4-dichloraniline, 2,6-dichloraniline, 3,5-dichloraniline, 2,4,5-, 2,4,6- and 3,4,5-trichloraniline, 4-bromaniline, 2-chloro-4-bromaniline, 2-methyl-4-chloraniline, 2-ethyl-4-chloraniline, 2-isopropyl-4-bromanilne, 2,4-dibromaniline, 2-methyl-4,5-dichloraniline, 2,4-, 3,4- and 2,6-dimethyl aniline, 2,6-diethyl aniline, 2,6-diisopropyl aniline, 4-methyl-2,6-diisopropyl aniline, 4-cyclohexenyl aniline, 2-, 3- or 4-nitroaniline, 2-chloro-4-nitroaniline, 2-chloro-4-nitroaniline, 3,5-dichloro-4-methoxy aniline, 3,5-dibromo-4-ethyl thioaniline, 3,5-dimethyl-4-chloraniline, 3,4-dimethoxy aniline, 2-chloro-5-dimethyl amidosulphonyl aniline, 2-chloro-5-cyano-aniline, 3,5-bistrifluormethyl aniline, 3-methyl-4-allyloxy aniline, 2-chloro-5-dimethyl amidocarbonyl aniline, 3-methyl-4-methoxy carbonyl aminoaniline, 2-chloro-4-methane sulphonyloxy aniline, 4-aminodiphenyl, 1-chloro-2-aminonaphthalene, 4-aminodiphenyl ether 4', 2,6-trichloro-4-aminodiphenyl ether, 4'-bromo-2,6-dimethyl-4-aminodiphenyl ether, 4',2-dichloro-4-aminodiphenyl ether, 4'-nitro-2,6-dichloro-4-aminodiphenyl ether, 4'-cyano-2,6-dibromo-4-aminodiphenyl ether, 4'-tert.-butyl-2,6-dichloro-4-aminodiphenyl ether, 4',2-dichloro-4-aminodiphenyl sulphide, 4'-chloro-2,6-dibromo-4-aminodiphenyl sulphide, 4'-dimethyl aminosulphonyl-2,6-dichlorodiphenyl ether, 4'2-dichloro-4-aminodiphenyl sulphoxide, 4',2-dichloro-4-aminodiphenyl sulphone, 4'2,6-trichloro-4-amino-diphenyl sulphone, 4',2,6-trimethyl-4-aminodiphenyl sulphone, 4'-chloro-4-aminobenzophenone, 4'-chloro-4-aminodiphenyl methane, 4-aminodiphenyl amine, 4'2,6-trichloro-4-aminodiphenyl amine, 4'-methoxy-2,6-dichloro-4-aminodiphenyl amine, 4'-cyano-2,6-dichloro-4-aminodiphenyl amine, 4'-methyl sulphonyl-2,6-dibromo-4-aminodiphenyl amine, 1,4-diaminobenzene, 1,3-diaminobenzene, 4,4'-diaminodiphenyl ether, 4,4'-diaminodiphenyl sulphone, 4,4'-diaminodiphenyl urea, 4,4'-diaminodiphenyl carbonate, preferably: Aniline, 4-chloraniline, 4-bromaniline, 3,4-dichloraniline, 4-aminodiaryl, ether, 4-aminodiaryl thioethers and 4-amino-diphenyl amines, 1-amino-naphthalene.

Reaction of the aryl amines with the 2,3-dihalogen acylisocyanates may be carried out in solvents which are inert to isocyanates under the reaction conditions. The following are examples of suitable solvents: hydrocarbons such as, for example, benzene, toluene, petroleum ether and petrol; chlorinated hydrocarbons such as, for example, dichloromethane, trichloromethane, 1,2-dichloroethane and tetrachloromethane; and ethers such as diethyl ether, diisopropyl ether, 1,2-dimethyloxy ethane, tetrahydrofuran and dioxan.

Benzene, toluene or others are preferably used.

The exothermic reaction is carried out at temperatures n the range of from $-20°$ to $+50°$ C and preferably at temperatures in the range of from $-10$ to $+20°$ C.

The reaction may be carried out, for example, by slowly adding a solution of the 2,3-dihalogen propionyl isocyanate dropwise with stirring and cooling to a solution of the aryl amine. The concentration of the 2,3-dihalogen propionyl isocyanate in the solvent is between 5 and 100% by weight and preferably between 10 and 80% by weight, whilst the concentration of the aryl amine is between 3 and 60% by weight and preferably between 5 and 40% by weight.

The 2,3-dihalogen propionyl isocyanate and the aryl amine are generally used in equimolar quantities, optionally with an excess of 1 to 5 mol % of 2,3-dihalogen acylisocyanate.

In another embodiment of the process according to the invention, a solution of the aryl amine is slowly added to a solution of the 2,3-dihalogen isocyanate under other wise the same reaction conditions.

The reaction is weakly exothermic and, if necessary, is completed by heating to between 30° and 50° C.

The N-aryl-N'-(2,3-dihalogen acyl)-ureas formed are substantially insoluble in the solvents mentioned and may be filtered off.

The process according to the invention for the production of 1-aryl-5-methylene-2,4-dioxoimidazolidines may even be carried out in a single operation, i.e. without intermediate isolation of the halogen acyl ureas.

The new 1-aryl-5-alkylidene-2,4-dioxoimidazolidines may be used as herbicides, fungicides, bactericides, nematocides or as coccidiostatics. They are intermediate products for the production of 1-aryl uracils which are important as herbicides and coccidiostatics.

EXAMPLE A

Seed dressing test/bunt of wheat (seed-born mycosis)

To produce a suitable dry dressing, the active compound was extended with a mixture of equal parts by weight of talc and kieselguhr to give a finely powdered mixture with the desired concentration of the active compound.

Wheat seed was contaminated with 5 g of the chlamydospores of *Tilletia caries* per kg of seed. To apply the dressing, the seed was shaken with the dressing in a closed glass flask. The seed, on moist loan under a cover of a layer of muslin and 2 cm of moderately moist compost soil, was exposed to optimum germination conditions for the spores for 10 days at 10° C in a refrigerator.

The germination of the spores on the wheat grains, each of which was contaminated with about 100,000 spores, was subsequently determined microscopically. The smaller the number of spores which had germinated, the more effective was the compound.

The active compounds, the concentrations of the active compounds in the dressing, the amounts of dressing used and the percentage spore germination can be seen from the following Table:

TABLE
Seed dressing test/bunt of wheat

| Active compounds | Active comp. concentration in dressing in % by wt. | Amount of dressing applied in g/kg of seed | Spore germination in % |
|---|---|---|---|
| not dressed | — | — | > 10 |
| 1-phenyl-5-methylene-2,4-dioxo-imidazolidine | 10 | 1 | 0,005 |
|  | 5 | 1 | 0,05 |
| 1-(3,4-dichloro-phenyl)-5-methylene-2,4-dioxo-imidazolidine | 10 | 1 | 0,5 |
| 1-(4-nitro-phenyl)-5-methylene-2,4-dioxo-imidasolidine | 10 | 1 | 0,5 |
| 1(4-chlorophenyl)-5-methylene-2,4-dioxo-imidazolidine | 10 | 1 | 0,005 |
|  | 5 | 1 | 0,05 |
| 1-naphthyl-(1)-5-methylene-2,4-dioxo-imidazolidine | 10 | 1 | 0,05 |
|  | 5 | 1 | 0,5 |
| Zineb (known comparison substance) | 10 | 1 | 5 |

In the following Examples all percentages are by weight unless otherwise specified.

EXAMPLE 1 a. 1-Phenyl-5-methylene-2,4-dioxoimidazolidine 20.0 g of the N-phenyl-N'-(2,3-dibromopropionyl)-urea prepared in accordance with Example 1(b) are suspended in 200 ml of tert.-butanol, 23 g of potassium tert.-butylate (90%) are introduced into the resulting suspension and the mixture is heated under reflux for 1 hour. The solvent is then distilled off under normal pressure and the residue is heated in vacuo for 20 minutes to 120° C. The white crystalline powder obtained is dissolved in 400 ml of water at 60° C and the solution is filtered and adjusted to pH 1 with dilute hydrochloric acid. The precipitated imidazolidine derivative is filered off, washed and dried. Yield: 9.0g m.p: 168° - 170° C (from methanol)

Analysis: $C_{10}H_8N_2O_2$ (molecular eight 188.18) Calculated: C, 63.82; H, 4.28; N, 14.89; 0.17.00; Found: C, 63.7; H, 4.3; N, 14.6; 0 -.

NMR/d-DMSO: 4.7 ppm (D, 1H) 5.2 (D, 1H) = methylene protons 7.5 (M, 5H)

IR/KBr: 1780, 1750 cm$^{-1}$(—CO— in a five ring)

b. N-phenyl-N'-(2,3-dibromopropionyl)-urea 9.5 g of aniline are dissolved in 100 ml of anhydrous benzene and a solution of 26.0 g of 2,3-dibromopropionyl isocyanate in 100 ml of benzene is added dropwise with cooling at 10 to 15° C. After stirring for 2 hours, the crystal sludge is diluted with the same volume of petroleum ether, filtered, washed with petroleum ether and dried. Yield: 30.0 g, m.p: 160°–161° C.

EXAMPLE 2 a. 1-(3,4-Dichlorophenyl)-5-methylene-2,4-dioxoimidazolidine 20.0 g of the urea derivative obtained in accordance with Example 2(b) are heated under reflux for 1 hour in 250 ml of tert.-butanol following the addition of 19.0 g of potassium tert.-butylate (90%), the solvent is distilled off and the residue is heated in vacuo for 20 minutes to 140° C. The reaction mixture is then dissolved in 500 ml of water at 80° to 90° C/pH 12, filtered and the reaction product is precipitated by the addition of dilute acetic acid. 11.0 g are obtained after filtration and drying. m.p.: 234° - 236° C (from glacial acetic acid).

Analysis: $C_{10}H_6Cl_2N_2O_2$ (molecular weight 257.09) Calculated: C, 64.72: H, 2.35; Cl, 27.58; N, 10.90; 0 12.45; Found: C, 46.5; H, 2.6; Cl, 27.5; N, 10.9; 0 - C, 46.6; H, 2.8 N, 11.1;

NMR/d-DMSO: 4.8 ppm (D, I - 2cs, III) 5.3 (D, I = 2cs) = methylene protons 7.4 (Q, 1H) 7.7 (D, 1H) 7.8 (D, 1H)

IR/KBr 3440 (NH) 1778 (—CO—)

b. N-(3,4-dichlorophenyl)-N'-(2,3-dibromopropionyl)-urea 16 g of 3,4-dichloroaniline are dissolved in 200 ml of dry benzene and a solution of 26.0 g of 2,3-dibromopropionyl isocyanate in 50 ml of benzene is added dropwise with cooling at 5° C. The urea formed is immediately precipitated in crystalline form. After stirring for 3 hours at 20° C, the reaction mixture is diluted with the same volume of petroleum ether, filtered and dried. Yield: 39.0 g, m.p: 174° - 175° C.

EXAMPLE 3 a. 1-(4-Nitrophenyl)-5-methylene-2,4-dioxoimidazolidine 20 g of the urea derivative obtained in accordanace with Example 3(b) are heated under reflux for 1 hour with 21.0 g. of potassium tert.-butylate (90%) in 200 ml of tert.-butanol, the solvent is distilled off and the residue is heated in vacuo for 20 minutes to 120° C. The reaction product is then dissolved at pH 12 in 500 parts by volume of water, filtered and the filtrate is precipitated with dilute hydrochloric acid. Yield after filtration and drying: 9.8 g, m.p.: 201° - 202° C (decomp.)

Analysis: $C_{10}H_7N_3O_4$ (molecular weight 233.19) Calculated; C, 51.51; H, 3.03; N, 18.02; O, 27.45; Found: C, 51.3; H, 3.4; N, 17.3; O - ; C, 51.6; H, 3.4; N, 17.5.

NMR/d-DMSO: 5.0 ppm (D, I = 2cs, 1H) 5.4 (D, I = 2cs, 1H) = methylene protons 7.7 (M, 2H) 8.4 (M, 2H)

IR/KBr 1775 - 1725 cm$^{-1}$(—CO— in 5-ring)

b. N-(4-nitrophenyl)-N'-(2,3-dibromopropionyl)-urea 14.0 g of 4-nitroaniline are dissolved in 200 ml of anhydrous acetonitrile, and 26.0 g of 2,3-dibromopropionyl isocyanate are added dropwise with cooling at 5° to 10° C. After stirring for 3 hours at 20° C, the solid precipitated is filtered off and dried. Yield: 35.0 g m.p.: 205° - 206° C (decomp.).

EXAMPLE 4 a. 1-(4-Chlorophenyl)-5-methylene-2,4-dioxoimidazolidine 25.0 g of the N-(4-chlorophenyl)-N'-(2,3-dibromopropionyl)-urea obtained in accordance with Example 4(b) are heated under reflux for 1 hour with 26.0 g of potassium tert.-butylate (90%) in 250 ml of tert.-butanol. The solvent is then distilled off under normal pressure and the residue is heated in vacuo for 20 minutes to 120° C. The reaction product is taken up with 500 ml of water at 60° C, precipitated with dilute acetic acid, filtered and dried. Yield: 12.0 g, m.p: 185° - 187° C.

Analysis: $C_{10}H_7ClN_2O_2$ (molecular weight 222.64) Calculated: C, 53.94; H, 3.17; Cl, 15.93; N, 12.59; O, 14.37; Found: C, 53.9; H, 3.2; Cl, 15.8; N, 12.5; O - C, 54.0; H, 3.2; Cl, 15.9; N, 12.8.

b. N-(4-chlorophenyl)-N'-(2,3-dibromopropionyl)-urea

A solution of 54 g of 2,3-dibromopropionyl isocyanate in 100 ml of benzene is added dropwise with cooling at 20° C to a solution of 25 g of 4-chloroaniline in 250 ml of dry benzene. After stirring for 3 hours at 20° C, the suspension is diluted with 200 ml of petroleum ether, filtered and dried. Yield: 71.0 g, m.p.: 162° – 163° C.

EXAMPLE 5 a. 1-(4-Ethoxyphenyl)-5-methylene-2,4-dioxoimidazolidine 70.0 g of the urea derivative obtained in accordance with Example 5(b) are heated under reflux for 30 minutes with 72.0 g of potassium tert.-butylate (90%) in 400 ml of tert.-butanol, the solvent is distilled off and the residue is heated in vacuo for 20 minutes to 120° C. The mixture is then taken up with 500 ml of hot water, filtered and the filtrate is acidified with dilute hydrochloric acid. Yield after filtration and drying: 30.0 g.

Analysis: $C_{12}H_{12}N_2O_3$ (molecular weight 232.24) Calculated C, 62.06; H, 5.21; N, 12.07; O, 20.67; Found C, 61.8; H, 5.3; N, 12.2; O, 20.5; C, 62.1; H, 5.4; N, 12.3; O, 20.8.

NMR/d-DMSO: 1.32 ppm (T, 3H) 4.06 (Q,2H) 4.55 (D,1H) 5.15 (D,1H) = $CH_2$ 7.0 (M, 2H) 7.3 (M, 2H) AA'BB' IR/KBr 3430 (OH) 3190 (NH) 1754 and 1732 (—CO—) 1645, 1509, 1248 $cm^{-1}$.

b. N-(4-ethoxy phenyl)-N'-(2,3-(dibromopropionyl)-urea 30.0 g of 4-ethoxy aniline are dissolved in 400 ml of dry benzene, and a solution of 57.0 g of 2,3-dibromopropionyl isocyanate in 200 ml of benzene is added dropwise with cooling at 0° to 5° C. On completion of the reaction, the suspension formed is diluted with an equal volume of petroleum ether, and the reaction product is filtered off and dried. Yield: 72.0 g, m.p.: 172° – 174° C.

EXAMPLE 6 a. 1-Naphthyl-(1)-5-methylene-2,4-dioxoimidazolidine 20.0 g of the urea derivative obtained in accordance with Example 6(b) are heated under reflux for 1 hour with 20.0 g of potassium tert.-butylate in 200 ml of tert.-butanol. The solvent is then distilled off and the residue is heated in vacuo for 20 minutes to 150° C. The reaction mixture is then taken up with 400 ml of water, filtered and precipitated by the addition of acid up to pH 2. Yield after filtration and drying: 9.1 g, m.p: 193° – 195° C (from methanol).

Analysis: $C_{14}H_{10}N_2O_2$ (molecular weight 238.24) Calculated C, 70.58; H, 4.23; N, 11.76; O, 13.43; Found C, 69.0; H, 4.4; N, 12.0; O - C, 69.3; H, 4.4; N, 12.0.

NMR/d-DMSO: 4.2 ppm (D, 1H) 5.2 (D, 1H) = $CH_2$; 7.5 – 8.1 (M, 9H)

IR/KBr: 1785 – 1720 $cm^{-1}$(—CO— in 5-ring)

b. N-(1-naphthyl)-N'-(2,3-dibromopropionyl)-urea 26.0 g of 2,3-dibromopropionyl isocyanate in 100 ml of toluene are added dropwise at 5 to 10° C to a solution of 14.5 g of 1-aminonaphthalene in 200 ml of dry benzene. After stirring for 2 hours at petroleum C, the reaction product is diluted with petroleum ether, filtered and dried. Yield: 35.0 g, m.p: 194° – 195° C (decomp.).

EXAMPLE 7

1-(3,4-Dichlorophenyl)-5-methylene-2,4-dioxoimidazolidine 16.0 g of 3,4-dichloroaniline are dissolved in 200 ml of anhydrous tetrahydrofuran, and a solution of 26 g of 2,3-dibromopropionyl isocyanate in 50 ml of benzene is added dropwise with cooling at 0° to 5° C. After stirring for 1 hour at 20° C, the reaction mixture is diluted with a further 200 ml of tetrahydrofuran, followed by the gradual introduction of 40 g of potassium tert.-butylate (90%). After heating under reflux for 1 hour, the solvent is distilled off under normal pressure and the residue is heated for 20 minutes to 120° C at 15 Torr. The residual solid is then dissolved in 1000 ml of water at 60° C and the solution is filtered, followed by precipitation by the addition of dilute hydrochloric acid. 18 g of product melting at 232° C to 235° C (from glacial acetic acid) are obtained after filtration and drying. The product obtained is identical with the imidazolidine derivative prepared in accordance with Example 2.

EXAMPLE 8 a. 1,4-Bis-(5-methylene-2,4-dioxoimidazolidinyl)-benzene 40 g of the urea derivative obtained in accordance with Example 8(b) are stirred with 400 ml of tert.-butanol, followed by the introduction of 53 g of potassium tert.-butylate (90%). After heating under reflux for 30 minutes, the solvent is distilled off under normal pressure and the residue is heated for 20 minutes to 120° C under 15 Torr. The reaction mixture is then dissolved with 300 ml of water at 60° C and the reaction product is precipitated by the addition of acetic acid. Yield: 16 g, m.p: 340° C (decomp).

NMR/d-DMSO: 4.78 ppm, 5.25 = $CH_2$ 7.52

IR/KBr: $3430^-$(NH 1750(—CO—, wide) 1644 (C=C) 1370, 836 $cm^{+1}$MS: $M^+$ 298.071 ME = $C_{14}H_{10}N_4O_4$ b. N,N-(Phenylene-1,4-bis-N',N'-(2,3-dibromopropionyl))-urea 15 g of 1,4-diaminobenzene are dissolved in 250 ml of dimethyl formamide and 72 g of 2,3-dibromopropionyl isocyanate are added dropwise at 0° C. After stirring for 3 hours at 20° C, the clear solution is poured into 2000 ml of ice water. The precipitated product is filtered off under suction, washed and dried. Yield: 76 g, m.p.: 215° C with decomp. (from acetone).

EXAMPLE 9 a. 1-(2,3-Dichlorophenyl)-5-methylene-2,4-dioxoimidazolidine 20 g of the N-(2,3-dichlorophenyl)-N'-(2,3-dichloropropionyl)-urea obtained in accordance with Example 9(b) are stirred with 200 ml of tert.-butanol and 23 g of potassium tert.-butylate (90%), heated to boiling point and the butanol is distilled off as far as possible over a period of 1 hour. The reaction mixture is then brought completely to dryness at 15 Torr and 100° C (bath temperature). The residue is dissolved with 300 ml of water (80° – 90° C), the solution is filtered until clear and the reaction product is precipitated by the addition of 20% acetic acid. The deposit is filtered off, washed with water until free from salt and dried. Yield: 11.0 g (70% of the theoretical amount), m.p.: 201° - 203° C after recrystallisation from dilute acetic acid. The elemental analysis and the nuclear resonance spectrum are consistent with the assumed constitution.

The following compounds may be similarly obtained from the acyl urea derivatives mentioned in Example 9(b):

1-(3,4-dichlorophenyl)-5-methylene-2,4-dioxoimidazolidine; m.p.: 230° - 233° C (identical with the compound of Example 2(a))

1-(4-chloro-2-methyl phenyl)-5-methylene-2,4-dioxoimidazolidine; m.p: 123° - 125° C 1-(2,4-dimethyl phenyl)-5-methylene-2,4-dioxoimidazolidine; m.p.: 163° - 165° C.

b.
N-(2,3-dichlorophenyl)-N'-(2,3-dichloropropionyl)-urea 16.0 g of 2,3-dichloroaniline are dissolved in 100 ml of dry benzene and a solution of 17.0 g of 2,3-dichloropropyl isocyanate in 20 ml of gasoline for cleaning (b.p. 80-110° C) is added dropwise at 10 to 15° C. The reaction product crystallises out after a short time. After stirring for 2 hours at 20° C, the product is filtered, washed with petroleum ether and dried. Yield: 25 g, m.p: 195° - 196° C.

The following compounds can be similarly obtained:

N-(3,4-dichlorophenyl)-N'-(2,3-dichloropropionyl)-urea; m.p: 145° - 148° C

N-(4-chloro-2-methyl phenyl)-N'-(2,3-dichloropropionyl)-urea; m.p: 147° - 149° C N-(2,4-dimethyl phenyl-N'-(2,3-dichloropropionyl-urea; m.p: 111° - 113° C N-(2,4-dichlorophenyl-N'-(2,3-dichloropropionyl)-urea; m.p: 174° - 176° C N-(2,4,5-trichlorophenyl)-N'-(2,3-dichloropropionyl)-urea; m.p: 180° °- 182° C N-(2,5-dichlorophenyl)-N'-(2,3-dichloropropionyl)-urea; m.p: 176° C N-(5-chloro-2-hydroxy phenyl)-N'-(2,3-dichloropropionyl)-urea; m.p: 177° - 179° C with decomposition N-(3-chloro-4-methyl phenyl)-N'-(2,3-dichloropropionyl)-urea; m.p: 130° - 131° C N-(4-chloro-3-methyl phenyl)-N'-(2,3-dichloropropionyl)-urea; m.p: 152° - 153° C N-(3,4-dichlorophenyl)-N'-(2,3-dibromobutyryl)-urea; m.p: 196° - 197° C (from 3,4-dichloroaniline and 2,3-dibromobutyryl isocyanate)

Preparation of halogenated acyl isocyanates of formula (III):

EXAMPLE 10a 100 g (1.41 mols) of acrylic acid amide are dissolved in 1200 ml of chloroform, and 224 g (1.41 mol) of bromine dissolved in 250 ml of chloroform are added dropwise with stirring to the resulting solution at a temperature of 0 to 5° C. The suspension formed is stirred for a further 5 hours at 20° C. 270 g (2.13 mols) of oxalyl chloride are then added dropwise with continued stirring, after which the reaction mixture is heated to boiling point and kept boiling under reflux until the evolution of gas is complete. The reaction mixture is then fractionally distilled, giving 220 g (61% of the theoretical amount) of 2,3-dibromopropionyl isocyanate boiling at 73° to 75° C/2.5 Torr.

EXAMPLE 10 b 99 g (1.40 mol) of chlorine are introduced with stirring at about 0 to 5° C into a solution of 100 g of acrylic acid amide in 1000 ml of chloroform. After stirring for 3 hours at about 20° C, 270 g (2.13 mol) of oxalyl chloride are added dropwise with continued stirring. The solution is then boiled under reflux until the evolution of gas is complete. Fractional distillation of the reaction solution gives 172 g (72% of the theoretical amount) of 2,3-dichloropropionyl isocyanate boiling at 38 to 41° C/1.0 Torr.

What is claimed is:

1. Process for preparing 1-aryl-5-alkylidene-2,4-dioxomidezolidines which comprises forming an N-aryl-N'-(2,3-dihalogen alkenoyl)-urea by a process comprising reacting a 2,3-dihalogen alkanoyl isocyanate having the formula

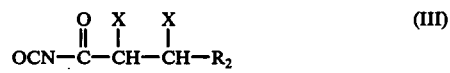

wherein
R₂ is hydrogen, in a solvent at a temperature in the range of from −20 to +50° C with a primary aryl amine of the formula R₁-NH₂
wherein
R₁ is phenyl or naphthyl which may be substituted one or more times by radicals selected from the group of hydrogen, C₁-C₆-alkyl, C₅ or C₆-acycloalkyl, C₁ or C₂-halogen substituted alkyl, C₁-C₆-alkoxy, C₁-C₆ thioalkyl and sulphoxide, C₁-C₆ alkyl sulphone, C₁-C₄ monoalkyl or dialkyl or diaryl-monoalkyl, C₁-C₆-acyl amino radical, cyclic amine radical in which the amino nitrogen atom is part of a 5 or 6 membered heterocycle which, in addition, may contain at least one further hetero atom as a ring member, said heterocycle being selected from the group consisting of pyrrolidino, 2-oxopyrrolidino, imidazolino and morpholno; cyano nitro, acetyl, aldehyde, phenyl, phenoxy, halogen phenoxy, nitro phenoxy, phenyl thio, benzyl, anilino, benzyl sulphenyl, phenyl sulphonyl and halogen-benzyl sulphonyl; and converting the urea that results, without intermediate isolation, to the imidazolidine by the process of contacting said N-aryl-N'-(2,3-dihalogen alkanol)-urea with an alkali metal alkoxide in a solvent at a temperature in the range of between 20° C and the boiling point of the solvent.

2. Process for preparing 1-aryl-5-alkylidene-2,4-dioxoimidozolidines which comprises reacting an N-aryl-N'-(2,3-dihalogen alkanoyl)-urea having the formula (II):

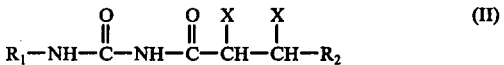

wherein
R₁ and R₂ are as defined in claim 1 and
X is chlorine or bromine,
with an alkali metal alkoxide in a solvent at a temperature in the range of between 20° C and the boiling temperature of the solvent.

3. Process of claim 2, wherein the temperature is from 60° to 140° C.

4. Process of claim 2 wherein the reaction is completed by distilling off the solvent and heating the residue under normal pressure or in vacuo to temperatures in the range of from 60° C to 180° C.

5. Process of claim 4 wherein the temperature is in the range of from 80° C to 140° C.

6. Process of claim 2 wherein the alkali metal alkoxide is potassium tert.-butylate.

7. Process of claim 2 wherein the solvent is tert.-butanol.

8. Process of claim 2 wherein the N-aryl-N'-(2,3-dihalogen-alkanoyl)-urea of general formula (II) is reacted with 2 to 4 mols of potassium tert.-butylate in tert.-butanol at temperatures in the range of from 20° C to 180° C.

9. Process of claim 8 wherein the temperature is in the range of from 60° to 150° C.

10. Process of claim 2 wherein the alcohol used to prepare the alkali metal alkoxide is employed as the solvent.

11. Process of claim 2 wherein the temperature is in the range of from 50° C to 120° C.

12. 1aryl-5-alkylidine-2,4-dioxoimidazolidine having the formula (I):

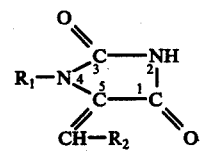

wherein
R₁ is phenyl, 3,4-dichlorophenyl, 4-nitro-phenyl, 4-chlorophenyl, 4-ethoxy-phenyl, naphthyl, 2,3-dichlorophenyl, -4-chloro-2-methyl-phenyl, 2,4-dimethyl and phenyl and
R₂ represents hydrogen.

* * * * *

UNITED STATES PATENT AND TRADEMARK OFFICE
CERTIFICATE OF CORRECTION

PATENT NO. : 4,036,850
DATED : July 19, 1977
INVENTOR(S) : Edgar Enders

Page 1 of 3

It is certified that error appears in the above-identified patent and that said Letters Patent are hereby corrected as shown below: Page 1 of 3 pages.

Column 1, line 27, "sulphono" should read -- sulphone --.

Column 2, line 34, "-5-phenyl" should read -- -3-phenyl --.

Column 2, line 46, "2mols" should read -- 2 mols --.

Column 3, line 38, "dbromopropionyl" should read
   -- dibromopropionyl --.

Column 4, line 9, "tetrahydro-1-1" should read
   -- tetrahydro-1 --.

Column 4, line 11, insert -- )) -- after "(1,3".

Column 5, lines 5 to 6, "alkanol" should read -- alkanoyl --.

Column 5, line 18, "if" should read -- If --.

Column 5, line 31, "(4chlorophenyl)" should read
   -- (4-chlorophenyl) --.

Column 5, line 46, "1-(3,5-...dioxoimidazolidine" should start a new line.

Column 5, line 49, "-4cyanophenyl" should read
   -- -4-cyanophenyl --.

Column 5, line 51, "5methylene" should read -- 5-methylene --.

Column 5, line 59, "1(2,4-)" should read -- 1-(2,4-) --.

Column 6, line 11, "1(3,4-)" should read -- 1-(3,4-) --.

Column 6, line 24, "1-[3,5...dine" should start a new line.

Column 6, line 31, "1[3,5-" should read -- 1-[3,5- --.

UNITED STATES PATENT AND TRADEMARK OFFICE
CERTIFICATE OF CORRECTION

PATENT NO. : 4,036,850

DATED : July 19, 1977

INVENTOR(S) : Edgar Enders

It is certified that error appears in the above-identified patent and that said Letters Patent are hereby corrected as shown below: Page 2 of 3 pages.

Column 6, line 50, "-doxo" should read -- -dioxo --.

Column 6, line 67, "1[5-" should read -- 1-[3- --.

Column 7, line 5, "1[3,5" should read -- 1-[3,5 --.

Column 7, line 5, "-4(4'" should read -- -4-(4' --.

Column 7, line 31, "alkylideno" should read -- alkylidene --.

Column 8, line 18, "others" should read -- ethers --.

Column 9, line 10, "oxapyrrolidino" should read -- oxopyrrolidino --.

Column 9, line 10, "imidazoline" should read -- imidazolino --.

Column 9, line 48, "4'2" should read -- 4',2 --.

Column 10, line 9, "n" should read -- in --.

Column 11, line 12, "imidasolidine" should read -- imidazolidine --.

Column 11, line 13, "1(4-" should read -- 1-(4 --.

Column 11, line 34, "filered" should read -- filtered --.

Column 11, line 37, "eight" should read -- weight --.

Column 12, line 1, "Cl 27.5" should read -- Cl 27.3 --.

Column 13, line 65, "petroleum" should read -- 20° --.

Column 14, line 39, delete "-" after "3430"

Column 14, line 40, "cm$^{+1}$" should read -- cm$^{-1}$ --.

UNITED STATES PATENT AND TRADEMARK OFFICE
CERTIFICATE OF CORRECTION

PATENT NO. : 4,036,850            Page 3 of 3
DATED : July 19, 1977
INVENTOR(S) : Edgar Enders It is certified that error appears in the above-identified patent and that said Letters Patent are hereby corrected as shown below:    Page 3 of 3 pages.

Column 16, lines 14 to 15, "dioxomidezolidenes" should read -- dioxomidazolidines --.

Column 16, line 31, "-acycloalkyl" should read -- -cycloalkyl --.

Column 16, line 41, "morpholno" should read -- morpholino --.

Column 16, line 41, insert "," after "cyano".

Column 16, line 44, "sulphenyl" should read -- sulphonyl --.

Column 16, line 48, "alkanol" should read -- alkanoyl --.

Column 16, line 53, "dioximidozolidines" should read -- dioxoimidazolidines --.

Column 18, line 6, "laryl" should read -- 1-aryl --.

Column 18, line 20, delete "and" between "dimethyl and phenyl".

Signed and Sealed this

Thirtieth Day of May 1978

[SEAL]

Attest:

RUTH C. MASON
Attesting Officer

LUTRELLE F. PARKER
Acting Commissioner of Patents and Trademarks